July 28, 1970 H. A. ROSS Plant Pat. 2,983

FLOWERING CRABAPPLE TREE

Filed July 5, 1968

INVENTOR
HENRY A. ROSS

BY
Oberlin, Maky, Donnelly & Renner
ATTORNEYS

United States Patent Office

Plant Pat. 2,983
Patented July 28, 1970

2,983

FLOWERING CRABAPPLE TREE

Henry A. Ross, Strongsville, Ohio, assignor to The Cole Nursery Company, Painesville, Ohio, a corporation of Ohio

Filed July 5, 1968, Ser. No. 742,985
Int. Cl. A01h *5/03*
U.S. Cl. Plt.—34 1 Claim

The present invention or discovery relates to a new and distinct variety of ornamental crabapple tree originated by me, having in combination novel coloration of bloom and habit of growth, and more particularly consists in a novel variety of Malus, var. Coralburst, flowering crabapple, having unusual and distinctive characteristics.

My new flowering crabapple tree is a small bushy tree of very slow dwarf growth which, in bloom, bears a very large number of small semi-double to double flowers of a soft pink color, the tightly closed buds being crimson. In order more quickly to obtain tree of greater height, my new variety may be top-grafted upon stock of the selected size. It has a pleasing upright form lacking the wide spreading habit of growth attributed to other dwarf varieties.

The novel and distinctive features of this new variety are accordingly considered to be, in combination:

(1) The dwarf habit of the tree; the original seedling clone was only about five (5) feet in height after ten to twelve years of growth.

(2) Such dwarft growth habit is accentuated by the relatively compact spacing of the branches and the stiff spur-like branchlets.

(3) The leaves are somewhat smaller than normal in flowering crabapple trees and have no purple cast.

(4) The flower buds are crimson in color.

(5) The semi-double to double flowers are produced very abundantly, even on very young and small plants.

(6) The flowers are soft pink in color without any purple tone, turning a somewhat lighter pink when old.

(7) The fruit is small and accordingly quickly disappears in the turf when it drops, avoiding the necessity of a clean-up operation.

(8) It comes into bloom when very young.

(9) The tree has been found to be very hardy in the neighborhood of Cleveland, Ohio.

There is a large demand for small ornamental flowering trees for landscape planting, and flowering crabapple trees have been recognized over a long period of time as especially suitable for such purposes. Eventually, however, most varieties of flowering crabapple trees tend to become overly large for use as dwarf varieties. Therefore, dwarf varieties are frequently preferred and much in demand. To the best of applicant's knowledge, however, a dwarf flowing crabapple tree has not heretofore been available with bloom in a clear soft pink color. The tree of the present invention is accordingly thought to serve a very useful horticultural purpose, having a more pleasing and harmonious color in flower and foliage than other crabapple trees (especially contrasted to those which are of a dull purplish color).

My new flowering crabapple tree has been propagated asexually at Painesville, Ohio, by budding and by grafting, and the tree can be very readily propagated in this manner, perpetuating all of its original characteristics. The original parent specimen was a seedling grown by me at Gardenview Horticultural Park, Strongsville, Ohio, and such original parent specimen was discovered and selected by me in a large plantation of crabapple tree seedlings grown by me from seeds selected from parent trees exhibiting some tendency towards certain of the desired characteristics.

Referring now more particularly to the drawing.

Figure 1:
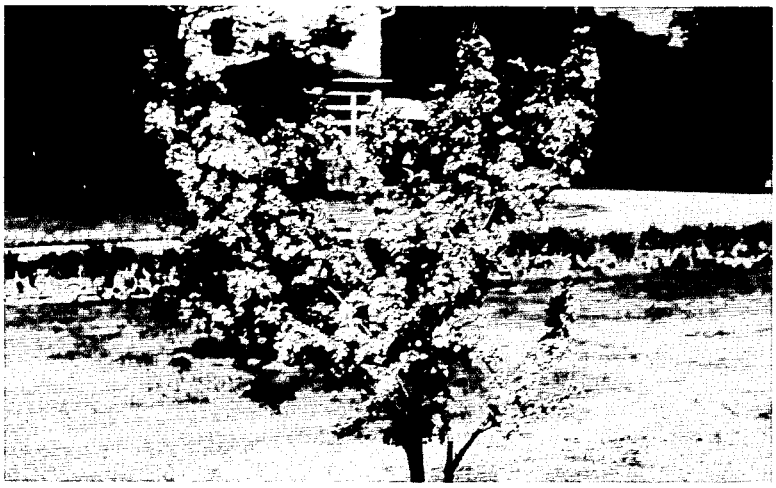
FIG. 1 shows my new flowering crabapple tree in the spring blooming season.
Figure 2:
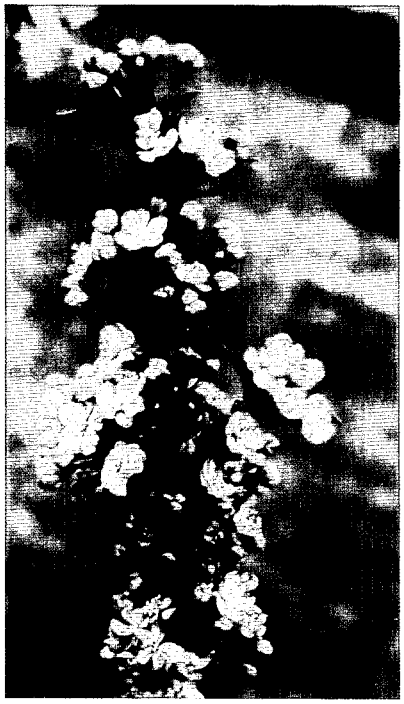
FIG. 2 shows a branchlet of such tree bearing a number of unopened flower buds.
Figure 3:
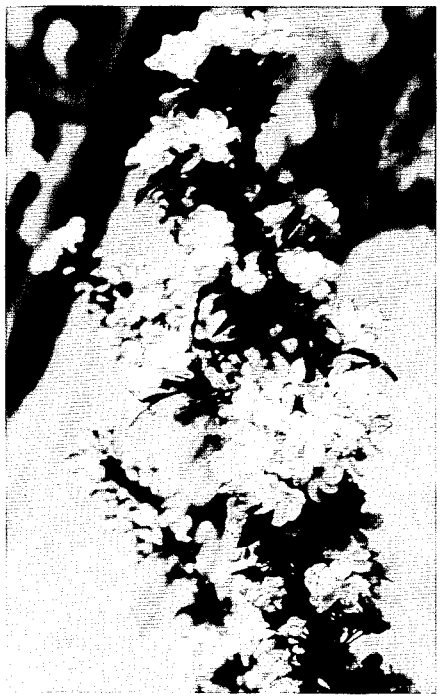
FIG. 3 shows a branchlet of such tree with a number of fully open flowers.

The following is a specific description of such new variety, color terminology in reference to the buds and flowers being in accordance with the Color Chart of the Royal Horticultural Society:

*Habit of growth.*—Dwarf, with stiff spreading branches forming a compact head. The tree is approximately 6 to 7 feet high when fully mature.

*Branches.*—The lateral branches are mostly short and spur-like with prominent lenticels. Young twigs are slightly hairy.

*Leaves.*—The leaves are small, 2.5–5 cm. long, about 12–24 mm. wide, wth finely and shallow crenate margins, dull green, slightly hairy above (approximately 2.5G 5/9 on the Nickerson Color Fan), lighter green, almost woolly beneath, especially when young. The petiole is short, about 15 mm. in length.

*Flowers.*—The semi-double to double flowers are small, produced very abundantly, even on small plants. The tight buds are Chrysanthemum Crimson 824/2, such buds being approximately ¼ inch wide and 5/16 inch long, although rather variable from season to season. When such buds are fully expanded they are Magenta Rose 027/1 and are approximately 7/16 inch wide and 5/16 inch long (as observed May 11, 1965, at Painesville, Ohio). The open flowers (as observed May 15, 1965, at Painesville, Ohio) have an inside petal color of Rhodamine Pink 527/2 and an outside petal color of Magenta Rose 027/1. Such flowers are composed of six to ten petals, 8–15 mm. long and 5–6 mm. wide, wth rounded tips. The sepals are small, and relatively narrow and pointed. The pedicels are 1½ to 2 cm. long.

*Fruit.*—The fruit is unostentatious, being about 1 cm. in diameter, nearly round, usually greenish to dull medium brown, and sometimes having a russet texture and color.

I claim:

1. A new and distinct variety of flowering crabapple tree, *Malus cultivar,* having a very dwarf and slow compact habit of growth contrasted to common flowering crabapple trees and most other dwarf flowering crabapple trees, and producing abundant tight crimson buds opening to semi-double to double flowers of soft pink color wth substantially no purple undertone.

No references cited.

ROBERT E. BAGWILL, Primary Examiner